US008318971B2

(12) United States Patent
Pohl et al.

(10) Patent No.: US 8,318,971 B2
(45) Date of Patent: Nov. 27, 2012

(54) PROCESS FOR PREPARING METHYLENEDIPHENYL DIISOCYANATES

(75) Inventors: Fritz Pohl, Brunsbüttel (DE); Andreas Bulan, Langenfeld (DE); Rainer Weber, Odenthal (DE); Richard Adamson, Leichlingen (DE); Matthias Böhm, Leverkusen (DE); Christian Six, Baytown, TX (US)

(73) Assignee: Bayer MaterialScience AG, Leverkusen (DE)

( * ) Notice: Subject to any disclaimer, the term of this patent is extended or adjusted under 35 U.S.C. 154(b) by 419 days.

(21) Appl. No.: 12/394,149

(22) Filed: Feb. 27, 2009

(65) Prior Publication Data
US 2009/0240076 A1 Sep. 24, 2009

(30) Foreign Application Priority Data

Mar. 1, 2008 (DE) .................... 10 2008 012 037

(51) Int. Cl.
C07C 249/00 (2006.01)

(52) U.S. Cl. ...................................... 560/347

(58) Field of Classification Search .............. None
See application file for complete search history.

(56) References Cited

U.S. PATENT DOCUMENTS

| | | | |
|---|---|---|---|
| 3,996,283 A | 12/1976 | Knofel | |
| 4,039,581 A | 8/1977 | Frulla et al. | |
| 4,250,114 A | 2/1981 | Biller | |
| 4,764,308 A | 8/1988 | Sauer et al. | |
| 4,798,909 A | 1/1989 | Biller | |
| 4,851,571 A | 7/1989 | Sauer et al. | |
| 5,931,579 A | 8/1999 | Gallus et al. | |
| 6,010,612 A * | 1/2000 | Freire et al. | 205/551 |
| 6,117,286 A | 9/2000 | Shimamune et al. | |
| 6,649,798 B2 | 11/2003 | Klein et al. | |
| 6,984,669 B2 | 1/2006 | Nishio et al. | |
| 7,105,700 B2 | 9/2006 | De Angelis et al. | |
| 7,408,083 B2 | 8/2008 | Steinbrenner et al. | |
| 2004/0024244 A1 | 2/2004 | Walsdorff et al. | |
| 2005/0118088 A1 | 6/2005 | Olbert et al. | |
| 2006/0123842 A1 | 6/2006 | Sohn et al. | |
| 2006/0252960 A1 | 11/2006 | Sohn et al. | |
| 2006/0263232 A1 | 11/2006 | Bulan | |
| 2007/0012577 A1 * | 1/2007 | Bulan et al. | 205/431 |
| 2007/0179316 A1 * | 8/2007 | Pohl et al. | 564/397 |
| 2008/0159948 A1 | 7/2008 | Sesing et al. | |
| 2009/0166180 A1 * | 7/2009 | Bulan et al. | 204/169 |

FOREIGN PATENT DOCUMENTS

| | | |
|---|---|---|
| DE | 2238920 A1 | 3/1974 |
| DE | 2426116 A1 | 1/1975 |
| DE | 2623681 A1 | 1/1977 |
| DE | 10260084 A1 | 7/2004 |
| DE | 1257522 B1 | 1/2006 |
| DE | 102005023615 A1 | 11/2006 |
| EP | 0291819 B1 | 7/1992 |
| EP | 1033419 A1 | 9/2000 |
| EP | 0830894 B1 | 12/2001 |
| EP | 1743882 A1 | 1/2007 |
| EP | 1813598 A1 | 8/2007 |
| EP | 1873142 A1 | 1/2008 |
| WO | WO 97/24320 A1 | 7/1997 |
| WO | WO-00/73538 A1 | 12/2000 |
| WO | WO-01/57290 A1 | 8/2001 |
| WO | WO-02/18675 A2 | 3/2002 |
| WO | WO-03/072237 A1 | 9/2003 |
| WO | WO-03/089370 A1 | 10/2003 |
| WO | WO-2004/014845 A1 | 2/2004 |
| WO | WO-2004/056756 A1 | 7/2004 |
| WO | WO-2005/007613 A1 | 1/2005 |
| WO | WO-2006/089877 A1 | 8/2006 |

* cited by examiner

Primary Examiner — Karl J Puttlitz
(74) Attorney, Agent, or Firm — Connolly Bove Lodge & Hutz LLP

(57) ABSTRACT

The invention relates to a process for preparing methylenediphenyl diisocyanates which comprises at least the steps: A) reaction of aniline with formaldehyde in the presence of hydrochloric acid as catalyst to give a mixture of diamines and polyamines of the diphenylmethane series (MDA) and subsequent at least partial neutralization of the hydrochloric acid by means of alkali metal hydroxide, B) reaction of the mixture of diamines and polyamines of the diphenylmethane series obtained in step A) with phosgene to give a mixture of diisocyanates and polyisocyanates of the diphenylmethane series (MDI) and hydrogen chloride, wherein C) the hydrochloric acid which has been neutralized in step A) is separated off in the form of a solution containing alkali metal chloride and is subsequently at least partly fed to an electrochemical oxidation to form chlorine, alkali metal hydroxide and optionally hydrogen and D) at least part of the chlorine produced in step C) is used for preparing the phosgene used in step B).

13 Claims, No Drawings

PROCESS FOR PREPARING METHYLENEDIPHENYL DIISOCYANATES

RELATED APPLICATIONS

This application claims benefit to German Patent Application No. 10 2008 012 037.5, filed Mar. 1, 2008, which is incorporated herein by reference in its entirety for all useful purposes.

BACKGROUND OF THE INVENTION

The invention proceeds from a process for preparing methylenediphenyl diisocyanates (MDI) by reacting aniline with formaldehyde in the presence of hydrochloric acid to give a mixture of diamines and polyamines of the diphenylmethane series and reacting the resulting mixture of diamines and polyamines of the diphenylmethane series with phosgene to give a mixture of diisocyanates and polyisocyanates of the diphenylmethane series.

Aromatic diisocyanates are important and versatile raw materials for polyurethane chemistry. Tolylene diisocyanate (TDI) and MDI are the most important industrial isocyanates here.

The general term "MDI" is used in the technical field and for the purposes of the present invention as collective term for methylene(diphenyl diisocyanates) and polymethylene-polyphenylene polyisocyanates, viz. the polyisocyanates of the diphenylmethane series. The polyisocyanates of the diphenylmethane series are, in particular, compounds and mixtures of compounds of the following type:

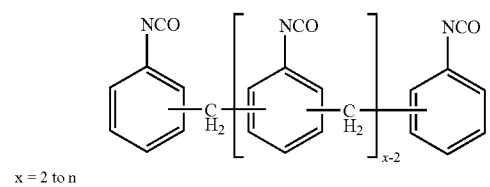

x = 2 to n where n is a natural number $\geq 2$.

The term methylene(diphenyl diisocyanate) encompasses the isomers 2,2'-methylene(diphenyl diisocyanate) (2,2'-MDI), 2,4'-methylene(diphenyl diisocyanate) (2,4'-MDI) and 4,4'-methylene(diphenyl diisocyanate) (4,4'-MDI). These isomers are referred to collectively as "monomeric MDI". The term polymethylene-polyphenylene polyisocyanates encompasses "polymeric MDI" (PMDI), which contains monomeric MDI and higher homologues of monomeric MDI.

In all industrially relevant production processes, MDI is obtained by phosgenation of the corresponding polyamines of the diphenylmethane series. The MDI synthesis is usually carried out in a two-stage process. Aniline is firstly condensed with formaldehyde to give a mixture of oligomeric and isomeric methylene(diphenyldiamines) and polymethylenepolyamines, known as crude MDA. This crude MDA is subsequently reacted in a second step with phosgene in a manner known per se to give a mixture of the corresponding oligomeric and isomeric methylene(diphenyl diisocyanates) and polymethylene-polyphenylene polyisocyanates, known as crude MDI. Here, the isomer and oligomer composition remains unchanged. Part of the 2-ring compounds is then usually separated off in a further process step, e.g. by distillation or crystallization, leaving polymeric MDI (PMDI) as residue.

The continuous, batchwise or semicontinuous preparation of polyamines of the diphenylmethane series, hereinafter also referred to as MDA for short, is described in numerous patents and publications (see, for example, H. J. Twitchett, Chem. Soc. Rev. 3(2), 209 (1974), M. V. Moore in: Kirk-Othmer Encycl. Chem. Technol., 3rd. Ed., New York, 2, 338-348 (1978). The preparation of MDA is usually carried out by reacting aniline and formaldehyde in the presence of acid catalysts. Hydrochloric acid is usually used as acid catalyst and the acid catalyst is, according to the prior art, neutralized and thus consumed at the end of the process and before the concluding work-up steps, for example the removal of excess aniline by distillation, by addition of a base, typically aqueous sodium hydroxide. In general, the addition of the neutralizing agent is carried out so that the resulting neutralisation mixture can be separated into an organic phase containing the polyamines of the diphenylmethane series and excess aniline and an aqueous phase containing sodium chloride together with residual organic constituents. The aqueous phase is generally disposed of as inorganically laden wastewater after removal of the organic constituents.

It is known that the composition of the crude MDA prepared by the process outlined, and consequently the crude MDI prepared therefrom, can be varied within a wide range by means of the reaction conditions employed. In this respect, the molar ratio of the components aniline and formaldehyde which are reacted (hereinafter also referred to as A/F ratio for short) and the amount of catalyst added, usually reported as degree of protonation (molar ratio of catalyst added to aniline fed in), are of particular importance.

High A/F ratios make it possible to obtain a crude MDA having a high monomer content, while high degrees of protonation promote the formation of 4,4'-MDA, which is of particular industrial importance as precursor for the corresponding 4,4-MDI. However, both measures lead to formation of large amounts of salts which firstly represents a large economic loss and secondly results in possible pollution of the environment.

There has been no lack of attempts to develop processes in which the wastewater obtained in the preparation of MDA and the salt burden to be disposed of via the wastewater are significantly reduced or avoided entirely.

DE 2 238 920 A1 discloses a process for preparing polyamines of the diphenylmethane series by condensing aniline with formaldehyde in the presence of water and acid catalysts, in which the fully reacted aqueous condensation mixture is extracted with a hydrophobic solvent, the resulting solvent phase is worked up to give the polyamines and the aqueous phase is, after addition of aniline and formaldehyde, recirculated to the beginning of the process. According to the teachings of DE 2 238 920 A1, the water of condensation formed in the reaction of the starting materials and excess water which gets into the system with the starting materials can be discharged from the system at a suitable point. Wastewater which contains essentially only the water introduced with the starting materials and that formed in the reaction of aniline with formaldehyde is obtained in the process; the use of sodium hydroxide is dispensed with. A disadvantage of this process is the use of an additional organic solvent whose use in an extraction and the removal by distillation require a large outlay in terms of apparatus and energy. In addition, large volumes of aqueous phase have to be circulated in the process and likewise have to be worked up by distillation.

The reduction of the aqueous phases to be worked up with simultaneous recirculation of the homogeneous catalyst used is subject matter of DE 2 426 116 A1. According to the teachings of DE 2 426 116 A1, it is particularly advantageous to carry out the reaction of aniline with formaldehyde in a number of stages and to react aniline and formaldehyde in a first stage in the absence of a catalyst to form a precondensate ("aminal"), separate off the water after the reaction is complete, then react the precondensate in the presence of acid salts of aniline or its condensation products with the formaldehyde in the presence of polar, organic solvents which remain inert under the reaction conditions and finally wash the catalyst used from the reaction mixture by means of water and recirculate it to the reaction stage of the precondensate. Here too, disadvantages are the use of an additional organic solvent and the high outlay in terms of apparatus and energy for extraction and distillation required as a result.

The intermediate formation of a precondensate is also disclosed by DE 2 623 681 A1, together with the use of a heterogeneous acid catalyst based on clay, zeolites or diatomaceous earths for the conversion of the precondensate into the polyamines of the diphenylmethane series. According to the teachings of DE 2 623 681 A1, the catalyst can be separated off from the polyamine mixture by filtration or centrifugation after the reaction is complete and recirculated to the reaction stage of the precondensate. However, for the rearrangement reaction, the aminal has to be subjected to complicated predrying, and a further disadvantage of the process is the accumulation of reaction products on the catalyst, which generally results in an unsatisfactory operating life of the catalyst.

Carrying out the conversion of the precondensate of aniline and formaldehyde into a two-ring MDA which is low in polymer using solid acid catalysts and at the same time utilizing the advantages of catalysis using solids having the sufficiently long catalyst operating lives required for industrial processes without obtaining appreciable residual amounts of polymeric MDA bases or incompletely rearranged intermediates ("aminobenzylanilines") in the end product is likewise subject matter of the teachings of EP 1 257 522 B1. However, disadvantages of the process disclosed in EP 1 257 522 B1 are likewise the costly drying necessary for the precondensate and the accumulation of reaction products on the catalysts used and the resulting short operating lives.

U.S. Pat. No. 7,105,700 B2, too, discloses the use of heterogeneous catalysts in the rearrangement of the aminals which are the primary reaction products of aniline with the formaldehyde added, using surface-modified zeolites as catalysts. However, according to the teachings of U.S. Pat. No. 7,105,700 B2, complicated predrying of the aminals is likewise necessary and the operating life of the catalysts used which is necessary for an industrial scale is achieved by the use of an additional solvent which has to be removed by distillation after the reaction is complete, which is likewise disadvantageous.

The advantages of homogeneous catalysis with simultaneous recovery of the acid catalyst in solid form is disclosed by WO 2005/007613 A1. WO 2005/007613 A1 discloses a process for preparing polyamines of the diphenylmethane series by reacting aniline with an agent which supplies methylene groups, in which the acid used as catalyst is removed from the reaction mixture by means of adsorption, e.g. on an ion exchanger, after the rearrangement reaction is complete and is subsequently recovered by regeneration of the adsorbent. A disadvantage of this process is the high outlay for complete adsorption and desorption of the catalyst used. To achieve complete removal of the catalyst from the reaction mixture, WO 2005/007613 A1 therefore discloses subsequent neutralization with customary basic neutralizing agents in order to remove last traces of acid, so that this known process also requires a high engineering outlay.

In summary, it can be said that in the processes known from the prior art which minimize the salt burden discharged with the wastewater, the outlay for the preparation of MDA becomes greater. In processes using heterogeneous catalysts, the operating life and regeneration of the catalysts generally present great problems, while in processes using homogeneous catalysts, the extraction processes require the use of additional materials and apparatuses. Standard processes using only small amounts of homogeneous catalyst do not give the desired breadth of the isomer composition, and aftertreatments which require a high outlay in terms of apparatus and energy are then required.

It is an object of the invention to discover an integrated process for preparing MDI, in which the wastewater obtained in the preparation of the precursor MDA and the salt burden to be disposed of via this wastewater outside the integrated process are significantly reduced or avoided entirely, without the outlay for the preparation of MDI increasing, without the yields, isomer ratios and homologue ratios and their control deteriorating and without the quality of the MDI obtained being adversely affected.

EMBODIMENTS OF THE INVENTION

An embodiment of the present invention is a process for preparing methylenediphenyl diisocyanate, comprising
  A) reacting aniline with formaldehyde in the presence of hydrochloric acid as catalyst to form a mixture of diamines and polyamines of the diphenylmethane series (MDA) and subsequently at least partially neutralizing said hydrochloric acid with alkali metal hydroxide;
  B) reacting said mixture of diamines and polyamines of the diphenylmethane series with phosgene to form a mixture of diisocyanates and polyisocyanates of the diphenylmethane series (MDI) and hydrogen chloride;
  wherein
  C) the hydrochloric acid neutralized in A) is separated off in the form of a solution comprising alkali metal chloride and at least a portion of which is subsequently fed directly to an electrochemical oxidation to form chlorine, alkali metal hydroxide, and optionally hydrogen; and
  D) at least part of the chlorine formed in C) is used to prepare the phosgene used in B).

Yet another embodiment of the present invention is the above process, wherein said alkali metal hydroxide in A) is sodium hydroxide.

Yet another embodiment of the present invention is the above process, wherein
  A1) water introduced with the starting materials or formed during the reaction of aniline with formaldehyde in the presence of hydrochloric acid as catalyst to form a mixture of diamines and polyamines of the diphenylmethane series (MDA) is optionally at least partly removed from the reaction mixture;
  A2) after neutralization of the reaction mixture formed in A1), an aqueous solution comprising alkali metal chloride and an organic phase comprising said mixture of diamines and polyamines is obtained;
  A3) the organic phase from A2) is separated off from the aqueous phase and worked up to give said mixture of diamines and polyamines; and A4) the aqueous solution comprising alkali metal chloride remaining after A3) is optionally at least partly combined with any water removed in A1) and/or with aqueous phases obtained in the work-up of said organic phase in step A3); purified; and at least partly fed to the electrochemical oxidation C).

Yet another embodiment of the present invention is the above process, wherein at least part of the alkali metal hydroxide formed in C) is recirculated to A) for neutralization of said hydrochloric acid.

Yet another embodiment of the present invention is the above process, wherein at least part of the hydrogen chloride formed in B) is converted into hydrochloric acid, at least part of which is used as said catalyst in A).

Yet another embodiment of the present invention is the above process, wherein the concentration of alkali metal chloride in the aqueous solution comprising alkali metal chloride formed in A) is from 2 to 24% by weight.

Yet another embodiment of the present invention is the above process, wherein the concentration of alkali metal chloride in the aqueous solution comprising alkali metal chloride formed in A) is from 5 to 15% by weight.

Yet another embodiment of the present invention is the above process, wherein said aqueous solution comprising alkali metal chloride is adjusted to a pH of <8 prior to purification in A4).

Yet another embodiment of the present invention is the above process, wherein said aqueous solution comprising alkali metal chloride is adjusted to a TOC value of <200 ppm, preferably <50 ppm, very particularly preferably <20 ppm, before the oxidation C).

The process of claim 1, wherein said aqueous solution comprising alkali metal chloride is adjusted to an alkali metal chloride content of >5% by weight, preferably >10% by weight, very particularly preferably >20% by weight, by removal of water and/or by addition of alkali metal chlorides in solid form or in the form of a concentrated solution before being used in an electrochemical oxidation.

Yet another embodiment of the present invention is the above process, wherein the aniline/formaldehyde reaction in A) is carried out at a degree of protonation of <30%, preferably <20%, particularly preferably <15% and very particularly preferably <10%.

Yet another embodiment of the present invention is the above process, wherein the electrochemical oxidation in C) is carried out as an alkali metal chloride electrolysis using ion exchange membranes and/or using gas diffusion electrodes as cathode.

Yet another embodiment of the present invention is the above process, wherein the alkali metal chloride electrolysis is carried out by the membrane electrolysis process using an ion exchange membrane, with the alkali metal chloride of the solution containing alkali metal chloride being sodium chloride and the ion exchange membrane having a water transport capacity of >3 mol of water/mol of sodium, preferably >4 mol of water/mol of sodium, particularly preferably >5 mol of water/mol of sodium.

Yet another embodiment of the present invention is the above process, wherein the alkali metal chloride solutions fed to the alkali metal chloride electrolysis are adjusted to a pH of <7, preferably pH <6, prior to electrolysis.

Yet another embodiment of the present invention is the above process, wherein the concentration of alkali metal chloride in the solution comprising alkali metal chloride leaving the electrolysis cell is from 100 to 280 g/l, preferably from 110 to 220 g/l.

Yet another embodiment of the present invention is the above process, wherein the concentration of the alkali metal hydroxide solution obtained from the electrolysis is from 13 to 33% by weight, preferably from 20 to 30% by weight.

DESCRIPTION OF THE INVENTION

The object could be achieved by the process of the invention. The invention provides a process for preparing methylenediphenyl diisocyanates, which comprises at least the steps
A) reaction of aniline with formaldehyde in the presence of hydrochloric acid as catalyst to give a mixture of diamines and polyamines of the diphenylmethane series (MDA) and subsequent at least partial neutralization of the hydrochloric acid by means of alkali metal hydroxide, preferably sodium hydroxide,
B) reaction of the mixture of diamines and polyamines of the diphenylmethane series obtained in step A) with phosgene to give a mixture of diisocyanates and polyisocyanates of the diphenylmethane series (MDI) and hydrogen chloride, characterized in that
C) the hydrochloric acid which has been neutralized in step A) is separated off in the form of a solution containing alkali metal chloride and is subsequently at least partly fed to an electrochemical oxidation to form chlorine, alkali metal hydroxide and optionally hydrogen and
D) at least part of the chlorine produced in step C) is used for preparing the phosgene used in step B).

For the purposes of the invention, methylenediphenyl diisocyanates are methylene(diphenyl diisocyanates) and polymethylene-polyphenylene polyisocyanates, viz. the polyisocyanates of the diphenylmethane series. The polyisocyanates of the diphenylmethane series are, in particular, compounds and mixtures of compounds of the following type:

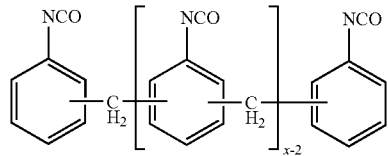

x = 2 to n where n is a natural number >2.

The novel process preferably has at least the following steps:
A1) reaction of aniline with formaldehyde in the presence of hydrochloric acid to give a reaction mixture containing diamines and polyamines of the diphenylmethane series ("MDA"), if appropriate at least partially with removal of the water introduced with the starting materials or formed in the reaction from the reaction mixture,
A2) neutralization of the reaction mixture formed in A1) using aqueous alkali metal hydroxide solutions to give an organic phase containing the mixture of diamines and polyamines of the diphenylmethane series and an aqueous solution containing alkali metal chloride,
A3) separation of the organic phase obtained in step A2) from the aqueous phase and work-up of the organic phase to isolate the mixture of diamines and polyamines of the diphenylmethane series (MDA),
A4) purification of the solution containing alkali metal chloride which remains after step A3) and has, if appropriate, been at least partly admixed with the aqueous phases removed from the reaction mixture in step A1) and/or with the aqueous phases obtained in the work-up of the organic phase in step A3), C) electrochemical oxidation of at least part of the solution containing alkali metal chloride from step A4), if appropriate after concentration and/or supplementation of the salt content by addition of the corresponding alkali metal chloride to form chlorine, alkali metal hydroxide and optionally hydrogen, D) preparation of phosgene by reaction of chlorine with carbon monoxide, B) reaction of the mixture of diamines and polyamines of the diphenylmethane series obtained in step A3) with the phosgene prepared in step D) to give a mixture of diisocyanates and polyisocyanates of the diphenylmethane series, with at least part of the chlorine prepared in step C) being fed to the preparation of phosgene in step D).

A further preferred variant of the novel process is characterized in that at least part of the alkali metal hydroxide prepared in C) is recirculated to the neutralization in step A).

The purification of the solution containing alkali metal chloride in step A4) is particularly preferably effected by stripping the solution with steam and subsequent treatment with activated carbon; the purification in step A4) is particularly preferably carried out after bringing the solution containing alkali metal chloride to a pH of less than or equal to 8, by stripping with steam and subsequent treatment with activated carbon.

In the integrated MDI process of the invention, all methods using hydrogen chloride catalyst as gas or in the form of hydrochloric acid which are known for the preparation of MDA and in which an aqueous solution containing alkali metal chloride is obtained can be employed in step A). The only essential criterion for the novel MDI process is that the solution containing alkali metal chloride which is obtained in the preparation of MDA is at least partly, preferably after a work-up, fed to an alkali metal chloride electrolysis and, if appropriate after removal of water or after appropriate supplementation with the corresponding alkali metal chloride, electrochemically oxidized there to produce chlorine and the chlorine formed is at least partly recirculated to the production of phosgene for the conversion of the polyamines into the corresponding polyisocyanates of the diphenylmethane series.

In a particularly preferred embodiment of the process of the invention, the preparation of MDA in step A) is carried out by the process disclosed in EP 1813 598 A1, which is hereby expressly incorporated by reference. EP 1 813 598 A1 discloses a process in which 1) aniline is reacted with formaldehyde in the presence of an acid catalyst to give a reaction mixture containing diamines and polyamines of the diphenylmethane series and 2) the reaction mixture containing diamines and polyamines is neutralized and 3) the neutralized reaction mixture containing diamines and polyamines is separated into an organic phase containing diamines and polyamines and an aqueous phase and 4) if appropriate, the organic phase is washed with water and 5) excess aniline is removed by distillation from the organic phase and 6) the wastewater and condensates obtained in steps 1)-5) are partly or completely combined, with at least the process water and condensates obtained in steps 3) and 5) being at least partly combined to give a mixture containing water, diamines and polyamines, aniline and salts of the catalyst used in step 1), and 7) the mixture obtained in step 6) is subjected to phase separation to give an aniline containing diamines and polyamines and 8) the aniline containing diamines and polyamines obtained in the phase separation is subsequently at least partly recirculated to the reaction in step 1).

In a very particularly preferred form of the process of the invention, a mixture containing water and from 0.001 to 5% by weight of MDA, from 0.5 to 60% by weight of aniline and I-25% by weight of salts of the acid catalyst used in step 1) in each case based on the weight of the mixture, is obtained in the preparation of MDA according to EP 1 813 598 in step 6), the process water obtained in this way is then extracted with aniline in a weight ratio of aniline to process water of 0.05-1:1, preferably 0.1-0.3:1, in an extraction, preferably a multistage extraction, at a temperature of from 30 to 120° C., preferably from 70 to 110° C., brought to a pH of less than or equal to 8 by addition of hydrochloric acid and aniline is finally removed from the extracted process water by distillation and/or by stripping with steam.

The particularly preferred form of the process of the invention which has just been outlined has the advantage that the resulting wastewater stream containing alkali metal chloride has already been largely freed of its organic constituents and no or only little work-up is required in order to use it in an alkali metal chloride electrolysis. However, as indicated above, all MDA processes in which an aqueous alkali metal chloride solution is obtained are suitable for the MDI process of the invention.

Regardless of the process employed for preparing the MDA, the aqueous salt solutions obtained in the preparation of MDA should be freed of organic impurities still present, in particular aniline, MDA and its precursors, formaldehyde, methanol and traces of phenol before use in the alkali metal chloride electrolysis. Methanol can get into the process as an impurity in formaldehyde and phenol can get in as an impurity in aniline. The purification can, for example, be carried out by extraction, by stripping with steam, by ozonolysis and driving-off of the carbon dioxide formed, adsorption on an adsorbent such as activated carbon or by other methods or by a combination of a number of methods.

Preference is given to a variant of the novel process in which the aqueous solution containing alkali metal chloride is brought to a TOC value of <200 ppm, preferably <50 ppm, very particularly preferably <20 ppm, before the oxidation C).

The purification of the solution containing alkali metal chloride which is obtained in the MDA processes employed can be carried out separately or, for example as indicated above, together with other water streams. The water streams obtained in the preparation of MDA are preferably combined and purified together; particular preference is given to setting the pH of the resulting solution to a value of less than or equal to 8 before the purification according to step A4).

In a preferred process, the pH is lowered by means of hydrochloric acid or hydrogen chloride. The use of the cheaper sulphuric acid which is conceivable in principle but undesirable in the process of the invention would lead in the lowering of the pH, namely the neutralization of the sodium hydroxide used in the neutralization in the preparation of MDA, to formation of sodium sulphate which would accumulate in the anolyte circuit in the subsequent electrolysis. Since, for example, the ion exchange membranes can, according to the information from the manufacturers, be operated only up to a particular sodium sulphate concentration, more anolyte would have to be discharged than when using hydrochloric acid or hydrogen chloride whose reaction product in the lowering of the pH is the desired sodium chloride.

In a further preferred embodiment of the invention, the alkali metal chloride concentration of the aqueous solution containing alkali metal chloride which is obtained from step A), in particular from step A4), is from 2 to 24% by weight, preferably from 5 to 15% by weight. In particular, the aqueous solution containing alkali metal chloride is brought to an alkali metal chloride content of >5% by weight, preferably >10% by weight, very particularly preferably >20% by weight, by removal of water and/or by addition of alkali metal chlorides in solid form or in the form of a concentrated solution before it is used in an electrochemical oxidation.

The alkali metal chloride electrolysis process will be described in more detail below. The following description of the electrolysis of sodium chloride should be regarded as illustrative since any alkali metal hydroxide can in principle be used in the neutralization of the reaction mixture of the preparation of MDA in the integrated MDI process of the invention, although the use of sodium hydroxide or the formation of sodium chloride in the preceding stages of the integrated MDI process of the invention is the preferred variant of the process.

Membrane electrolysis processes are usually used for the electrolysis of solutions containing sodium chloride (see Peter Schmittinger, CHLORINE, Wiley-VCH Verlag, 2000, pages 77-115). Here, a divided electrolysis cell comprising an anode chamber having an anode and a cathode chamber having a cathode is used. Anode chamber and cathode chamber are separated by an ion exchange membrane.

A solution containing sodium chloride and having a sodium chloride concentration of usually more than 300 g/l is introduced into the anode chamber. The chloride ion is oxidized to chlorine at the anode and the chlorine is discharged from the cell together with the depleted sodium chloride solution (about 200 g/l). The sodium ions migrate under the action of the electric field through the ion exchange membrane into the cathode chamber. Each mole of sodium carries water with it in the membranes usually used.

A "dilute" sodium hydroxide solution is usually fed into the cathode chamber. At the cathode, water is electrochemically reduced to form hydrogen and hydroxide ions. This reaction consumes water on the cathode side of the cell and produces "additional" sodium hydroxide as a result of the hydroxide ions remaining in the cathode chamber and the sodium ions which get into the cathode chamber via the ion exchange membrane. As an alternative, it is also possible to use a gas diffusion electrode as cathode, in which case oxygen is converted by means of electrons into hydroxide ions and no hydrogen is formed at the cathode. It is possible to use, for example, gas diffusion electrodes as described in DE 10 2005 023615 A1. The operation of the gas diffusion electrode can be carried out as described in EP 1 033 419 A1, U.S. Pat. No. 6,117,286 B2 or WO 2001/057290 A1.

Preference is therefore given to a process which is characterized in that the electrochemical oxidation in step C) is carried out in the form of an alkali metal chloride electrolysis using ion exchange membranes and/or using gas diffusion electrodes as cathode.

It is usually an objective to achieve very high concentrations of sodium hydroxide, since commercial sodium hydroxide is stored and transported as a 50% strength by weight solution. However, commercial membranes are at present not resistant to a sodium hydroxide solution having a concentration higher than about 35% by weight, so that the sodium hydroxide solution has to be concentrated by thermal evaporation. When commercial membranes are used, a substream of the "concentrated" sodium hydroxide solution produced is usually discharged and the remaining stream is diluted with water and recirculated to the cathode side of the sodium chloride electrolysis while maintaining the sodium hydroxide concentration in the outflow from the cell at 31-32% by weight, at an inflow concentration of the sodium hydroxide solution of about 30% and a current density of 4 kA/m$^2$.

In the sodium chloride electrolysis outlined, water is introduced into the anolyte via the solution containing sodium chloride, but only water is discharged through the membrane into the catholyte. If more water is introduced via the solution containing sodium chloride than can be transported through the membrane into the catholyte, the anolyte becomes depleted in sodium chloride and the electrolysis cannot be operated continuously since the secondary reaction of oxygen formation would commence at very low sodium chloride concentrations. To avoid this secondary reaction, the electrolysis using customary membrane electrolysis cells is operated so that the anolyte discharged from the cell has a concentration of about 200 g/l of sodium chloride, the concentration of the anolyte discharged is then increased again to the intended concentration of about 300 g/l by addition of solid sodium chloride or a highly concentrated sodium chloride solution and recirculated to the anode chamber. To avoid accumulation of undesirable constituents, it can be advantageous to discharge a substream of 1-5% of the depleted anolyte stream.

In a preferred embodiment of the integrated MDI process of the invention, a particularly economical use of the solutions containing sodium chloride which are obtained in the preparation of MDA is achieved by, after concentration of the solutions containing sodium chloride, increasing the water transport through the membrane in their electrolysis. This is achieved by the choice of suitable membranes as described, for example, in U.S. Pat. No. 6,984,669 B2, with use being made of ion exchange membranes which have a water transport per mole of sodium of more than 3 mol of $H_2O$/mol of sodium, preferably >4 mol of $H_2O$/mol of sodium, particularly preferably >5 mol of $H_2O$/mol of sodium.

Preference is consequently given to an embodiment of the process which is characterized in that the alkali metal chloride electrolysis is carried out by the membrane electrolysis process using an ion exchange membrane, with the alkali metal chloride of the solution containing alkali metal chloride being sodium chloride and the ion exchange membrane having a water transport capacity of >3 mol of water/mol of sodium, preferably >4 mol of water/mol of sodium, particularly preferably >5 mol of water/mol of sodium.

The effect of the increased water transport is, firstly, that the otherwise customary addition of water to maintain the alkali metal hydroxide concentration can be dispensed with and, secondly, that an improved conversion of the sodium chloride used is achieved at the same outflow concentration. Thus, for example, when a membrane having a water transport of 6.0 mol of $H_2O$/mol is used at a feed concentration of the solution containing sodium chloride of 24% by weight and an outflow concentration of 16.3% by weight, an alkali metal hydroxide concentration of 30.4% by weight and a recycling ratio of NaCl in a single pass of 66%, in the case of recirculation a recycling ratio of virtually 100% are achieved. To achieve this, it is necessary for the NaCl to be present in a concentration of 24 in an aqueous solution and the depleted NaCl solution coming from the cell to be recirculated and be brought to a concentration of 24% by weight by means of solid NaCl before it is reused. To avoid accumulation of impurities, about 1% of the depleted NaCl solution coming from the cell is discharged from the process.

A further possible way of influencing the water transport is to modify the operating conditions of the electrolysis of the NaCl solutions so that the NaCl concentration is reduced and/or the sodium hydroxide concentration is reduced. It is likewise conceivable for increased water transport to take place at a low brine concentration and a low sodium hydroxide concentration. A further possibility is to increase the current density of the electrolysis in order to make higher water transport possible. This can also be carried out at altered concentrations of sodium hydroxide and NaCl solution. This is preferably done when anodes having a relatively large internal surface area are used, so that the local current density is significantly lower.

In the preferred form of the novel MDI process using ion exchange membranes having a water transport capacity of >4.0 mol of $H_2O$/mol of sodium which has been outlined, the current density based on the membrane area is, in particular, from 2 to 6 $kA/m^2$. Particular preference is given to using anodes having a relatively large surface area. For the purposes of the present invention, anodes having a relatively large surface area are ones in which the physical surface area is significantly higher than the geometric surface area, i.e. calculated from the external dimensions of the electrode. Anodes having a relatively large surface area are, for example, electrodes having a foam-like or felt-like structure. In this way, a very large electrode surface area is offered anodically and the local current density is greatly reduced. The surface area of the anode is preferably selected so that the local current density based on the physical surface area of the electrode is less than 3 $kA/m^2$. The larger the surface area and the lower the local current density, the lower the sodium chloride concentration of the brine can be made and the higher the proportion of sodium chloride from the brine which can be recycled as anolyte in one pass of the brine.

The alkali metal chloride electrolysis in step C) should particularly preferably be operated so that the alkali metal chloride concentration of the alkali metal chloride solution leaving the cell is from 100 to 280 g/l of sodium chloride and/or the concentration of the alkali metal hydroxide solution leaving the cell is from 13 to 33% by weight. Very particular preference is given to concentrations which allow operation of the cell at a relatively low voltage. For this purpose, the concentration of the alkali metal chloride solution leaving the cell should preferably be in the range from 110 to 220 g/l of alkali metal chloride and/or the concentration of the alkali metal hydroxide solution leaving the cell should preferably be from 20 to 30% by weight.

In the novel integrated MDI process using sodium chloride electrolysis, the electrolysis is preferably operated at a temperature of from 70 to 100° C., more preferably from 80 to 95° C., and an absolute pressure of, in particular, from 1 to 1.4 bar, preferably an absolute pressure of from 1.1 to 1.2 bar, with the pressure ratios between anode chamber and cathode chamber being selected, in particular, so that the pressure in the cathode chamber is higher than the pressure in the anode chamber. In a particularly preferred embodiment, the pressure difference between cathode chamber and anode chamber is from 20 to 150 mbar, very particularly preferably from 30 to 100 mbar.

At a relatively low alkali metal chloride concentration, it is also possible to use special anode coatings. In particular, the coating of the anode can contain ruthenium oxide together with further noble metal components of transition groups 7 and 8 of the Periodic Table of the Elements. For example, the anode coating can be doped with palladium compounds. Coatings based on diamonds can likewise be used.

If the alkali metal chloride electrolysis in the novel MDI process is used solely for the work-up of the solutions containing alkali metal chloride which are obtained in the preparation of MDA, these solutions should be concentrated, preferably to an alkali metal chloride concentration of >10% by weight, by addition of alkali metal chloride or by removal of water before they are used in the electrolysis. In the case of the removal of water, the solutions containing sodium chloride which are obtained in the preparation of MDA are preferably concentrated by means of membrane processes, for example by reverse osmosis or membrane distillation processes (see MELIN; RAUTENBACH, Membranverfahren; SPRINGER, BERLIN, 2003, pages 495-530). The combination of operation according to the invention of the electrolysis cells and concentration processes theoretically enables up to 100% of the sodium chloride to be recovered from the NaCl-containing waters from the preparation of MDA.

The chlorine produced in the alkali metal chloride electrolysis is worked up in a known manner (see Ullmann's Enzyklopädie der technischen Chemie, 6th edition, volume 8, pages 254-265) and then fed at least partly to the phosgene synthesis of the integrated MDI process of the invention.

The phosgenation of the MDA produced by the novel integrated MDI process requires more chlorine than is obtained by electrolysis of the HCl catalyst which is used in the preparation of MDA and has been recovered in the form of an aqueous solution containing alkali metal chloride. Thus, at an A/F ratio of 3 and a degree of protonation of 30%, about 25% of the chlorine required can be obtained from the recirculation and electrochemical oxidation of the neutralized catalyst, but at the same A/F ratio and a degree of protonation of 20%, only about 17%. Further chlorine therefore has to be provided for the phosgene synthesis in the novel process.

The provision of additional chlorine can be effected by all known methods of the prior art, e.g. by introduction of externally procured chlorine or by means of a preparation of chlorine from the hydrogen chloride obtained in the preparation of MDI by direct oxidation by the Deacon process or after conversion of the hydrogen chloride into hydrochloric acid and electrolysis of the latter by the diaphragm process or electrolysis using a gas diffusion electrode as cathode operated in conjunction with the preparation of MDI. Suitable processes are described, for example, in WO 2004/014845 A1 ("Integriertes Verfahren zur Herstellung von Isocyanaten und katalytische Oxidation von Chlorwasserstoff nach dem Deacon-Verfahren"), WO 2000/073538 A1 and WO 2002/018675 A2 ("Elektrochemische Oxidation einer wässrigen Lösung von Chlorwasserstoff unter Verwendung einer Gasdiffusionselektrode als Kathode") and especially in EP 1 743 882 A1 ("Integriertes Verfahren zur Herstellung von Isocyanaten aus Phosgen und wenigstens einem Amin und elektrochemische Oxidation des dabei anfallenden Chlorwasserstoffs zu Chlor, wobei das Chlor zur Herstellung des Phosgens rtlickgeführt wird"), but other electrochemical recycling processes are also suitable.

However, the additional chlorine required can also be provided by means of an appropriately dimensioned alkali metal chloride electrolysis, with the hydrogen chloride formed in the MDI synthesis which is not required as catalyst in the preparation of MDA in the integrated novel MDI process then being able to be used as starting material for an EDC process or converted into chlorine according to the prior art by means of an electrochemical recycling process or be absorbed in water and passed as hydrochloric acid to another use. An overview of suitable electrochemical recycling processes is given in the article "Chlorine Regeneration from Anhydrous Hydrogen Chloride" by Dennie Turin Mab, published in "12th International Forum Electrolysis in Chemical Chemistry—Clean and Efficient Processing Electrochemical Technology for Syntheses, Separation, Recycle and Environmental Improvement, Oct. 11-15, 1998. Sheraton Sand Key, Clearwater Beach, Fla.".

The provision of the additional chlorine required is preferably carried out in an alkali metal chloride electrolysis dimensioned so as to allow use of virtually all the aqueous alkali metal chloride solutions which are obtained in step A of the preparation of MDA in the integrated MDI process of the invention and have subsequently been largely freed of their organic impurities by extraction, steam stripping and treatment with activated carbon to prepare the brine solutions, with, in a very particularly preferred embodiment, the dilution water required for the sodium hydroxide solution formed on the cathode side of the sodium chloride electrolysis being covered firstly by the water transported with the sodium ions to the cathode side and secondly by the water of the wastewater stream obtained in the preparation of MDA in the integrated MDI process of the invention. This complete use is achieved especially at a low (<30%) degree of protonation in the preparation of MDA in the novel integrated MDI process; preference is given to a degree of protonation of <20%, particularly preferably <15%, very particularly preferably <10%. The combination of the use of specific ion exchange membranes which, compared to the conventional prior art, allow transport of a large amount of water through the membranes and the low degrees of protonation according to the invention in the preparation of MDA consequently leads to a particularly preferred form of the novel integrated MDI process. This particularly preferred form is characterized in that, if purge amounts are disregarded, complete recycling of the acid catalyst used in the preparation of MDA is achieved, the wastewater stream obtained as wastewater containing sodium chloride in the preparation of MDA can at the same time all be used in the NaCl electrolysis and all be utilized there as dilution water in the preparation of sodium hydroxide, so that in the novel integrated MDI process no wastewater obtained in the preparation of MDA has to be discharged for treatment outside the integrated MDI process.

In a further preferred embodiment, the additional chlorine required is provided in an alkali metal chloride electrolysis and an HCl electrolysis, with the dimensioning of the alkali metal chloride electrolysis allowing use of all of the aqueous alkali metal chloride solutions which are obtained in step A of the preparation of MDA in the integrated MDI process of the invention and have subsequently been largely freed of their organic impurities by extraction, steam stripping and treatment with activated carbon for provision of the brine solutions, the chlorine additionally required being provided by means of an HCl electrolysis by the diaphragm process and/or using a gas diffusion electrode as cathode and the chlorine formed in the alkali metal chloride electrolysis and the HCl electrolysis being worked up in a joint work-up for use in the production of phosgene in the integrated MDI process of the invention.

The chlorine which has been provided in the required amount is reacted with carbon monoxide to form phosgene, for which it is possible to use the processes known from the prior art, as are described, for example, in Ullmanns Enzyklopädie der industriellen Chemie, 3rd edition, volume 13, pages 494-500. The reaction of carbon monoxide and chlorine over activated carbon as catalyst at temperatures of from 250° C. up to a maximum of 600° C. which is customary on the industrial scale is preferred, with shell-and-tube reactors particularly preferably being used. The heat of reaction of the strongly exothermic reaction can be removed in various ways, for example by means of a liquid heat-transfer medium as described in, for example, WO03/072237 A1 or by evaporative cooling via a secondary circuit with simultaneous utilization of the heat of reaction for generation of steam, as disclosed, for example, in U.S. Pat. No. 4,764,308 A.

The reaction of phosgene with polyamines of the diphenylmethane series is carried out on an industrial scale and has been described many times (see, for example, Kunststoffhandbuch, volume 7 (Polyurethane), 3rd revised edition, Carl Hanser Verlag, Munich-Vienna, p. 76 ff (1993)). For the integrated MDI process of the invention, all liquid-phase phosgenation processes known from the prior art are suitable. The reaction of the polyamines of the diphenylmethane series produced in step A) of the novel process is preferably carried out by the processes disclosed WO 2004/056756 A1 and EP 1 873 142 A1, which are hereby expressly incorporated by reference. The reaction of the polyamines of the diphenylmethane series produced in step A) is particularly preferably carried out by the process disclosed in EP 1 873 142 A1.

The process disclosed in EP 1 873 142 A1 comprises reaction of the polyamines of the diphenylmethane series with phosgene in at least three stages, with the first stage being carried out in a dynamic mixer, the second stage being carried out in at least one reactor and the third stage being carried out in at least one separation apparatus and with the pressure in the second stage being greater than or equal to the pressure in the dynamic mixer and the pressure in the at least one separation apparatus being lower than the pressure in the reactor of the second stage.

According to the teachings of EP 1 873 142 A1, the reaction occurring in the first phosgenation stage of the process disclosed is essentially the reaction of the primary amine groups of the polyamines of the diphenylmethane series used to form carbamoyl chlorides and amine hydrochlorides, the reaction in the second stage is essentially the conversion of the amine hydrochlorides formed in the first stage into carbamoyl chlorides and the reaction in the third stage is essentially the dissociation of the carbamoyl chlorides into isocyanate groups and hydrogen chloride. In the process disclosed in EP 1 873 142 A1, the reaction of the amine with the phosgene is carried out in an inert solvent, preferably toluene or chlorobenzene, dichlorobenzene or mixtures thereof, using an excess of phosgene.

According to the teachings of EP 1 873 142 A1, the first phosgenation stage is carried out in a dynamic mixer, preferably in mixer reactors whose function is described, for example, in EP 0 291 819 B1 in column 1/line 44 to column 2/line 49 and whose detailed structure is described in combination with FIGS. 1 and 2 in column 4/line 34 to column 5/line 46, particularly preferably in mixing reactors whose function is described in EP 0 830 894 B1 in paragraphs 0005 to 0011/0012 to 0014 and whose detailed structure is described in combination with FIGS. 1 to 4 in paragraphs 0016 to 0022. However, all dynamic mixers which ensure intensive mixing by means of mechanical moving parts, for example rotary mixing apparatuses and in particular multistage centrifugal pumps, are suitable for use in the first phosgenation stage.

When used in the novel integrated MDI process, the pressure in the dynamic mixer of the first phosgenation stage is, in particular, preferably from 3 to 70 bar, particularly preferably from 3 to 35 bar. The temperature in the first stage is preferably from 80 to 220° C., particularly preferably from 90 to 180° C., with the reaction in the first stage preferably being carried out adiabatically.

In a manner analogous to the process disclosed in EP 1 873 142, the second phosgenation stage in the novel integrated MDI process is carried out in at least one reactor, i.e. a residence apparatus suitable for carrying out chemical reactions, which is connected hydraulically to the dynamic mixer of the first stage. The pressure in the second phosgenation stage is preferably from 3 to 70 bar, particularly preferably from 3 to 37 bar. The temperature in the second stage is preferably from 80 to 220° C., particularly preferably from 90 to 180° C. Possible reactor types for the second stage are tube reactors, stirred vessels or unmixed residence apparatuses. The reactor can also be provided with a pumped circuit which can in turn contain a heat exchanger for adjusting the reactor temperature. The use of tube reactors is particularly preferred.

According to the teachings of EP 1 873 142 A1, the carbamoyl groups are converted into isocyanate groups and the reaction mixture is separated into a gas phase and a liquid phase in the third phosgenation stage of the process disclosed in EP 1 873 142 A1. The gas phase contains essentially hydrogen chloride and may, depending on pressure and temperature, contain part of the phosgene used in excess and solvent vapour. In a manner analogous to the process disclosed in EP 1873 142 A1, the third phosgenation stage in the novel integrated MDI process is preferably operated at a pressure of from 0.5 to 20 bar, particularly preferably from 0.5 to 16 bar, with the reaction mixture being depressurized to the pressure of the separation apparatus by means of a valve or another device suitable for this purpose downstream of the reactor of the second phosgenation stage and the temperature of the third phosgenation stage being set to from 80 to 220° C.

Suitable reactors for the separation apparatus of the third phosgenation stage in the novel integrated MDI process are heat exchangers with a separate gas outlet and also stirred vessels, cascades of stirred vessels, perforated plate columns or other apparatuses for phase separation, with particular preference being given to a (reaction) tower as described in DE 37 36 988 C1/column 3, lines 2-64. The separation apparatus in the third phosgenation stage can also be utilized for removing the excess phosgene from the reaction mixture. The separation apparatus of the third stage can likewise be disadvantageously large. In this case, the separation apparatus of the third stage can also be realised by means of two or more identical or different apparatuses, preferably a combination of heat exchangers having a separate gas outlet and (reaction) tower or (reaction) tower/towers and (reaction) column, which are preferably connected in series.

The reaction mixture discharged from the phosgenation is subsequently worked up by the customary methods for removing any phosgene still present and for separating off the solvent. Further purification steps can follow.

Phosgene, hydrogen chloride and solvent are then separated off in a known manner from the vapour produced in the phosgenation and the vapour produced in the downstream dephosgenation and, if appropriate, recirculated to suitable points in the process. The vapours are preferably combined before being worked up and only then separated into the components, preferably using the method disclosed in DE 102 60 084 A1, which is expressly incorporated by reference.

As indicated above, the hydrogen chloride obtained in the novel integrated MDI process can, if appropriate after additional purification, be converted into chlorine by the Deacon process or after conversion into hydrochloric acid by electrolysis of the latter; it is likewise possible for it to be used in an EDC process or be passed on in the form of hydrochloric acid.

In a preferred embodiment of the novel integrated MDI process, a substream of the hydrogen chloride produced in the phosgenation is used, preferably in the form of a 25-30% strength by weight hydrochloric acid, as catalyst in the preparation of MDA in the integrated process and the remaining hydrogen chloride is purified further and passed as described above to an electrochemical recycling process for the preparation of chlorine. The further purification of the hydrogen chloride is preferably carried out by one of the processes disclosed in WO 2003/089370 A1 and WO 2006/089877 A1, with both processes being employed in a serial arrangement in a particularly preferred form.

The embodiments of the stages of the integrated MDI process of the invention which have been described by way of example in the above chapters can be carried out individually in another way known in principle to those skilled in the art without the novelty according to the invention being affected thereby.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Example 1

12.22 t/h of a mixture containing proportionately wastewater and condensates from the stages of a preparation of MDA comprising the following steps, namely a) aniline and formaldehyde are reacted in an A/F ratio of 3 in the presence of 30% strength by weight hydrochloric acid as catalyst at a degree of protonation of 10%,
b) the reaction mixture is neutralized with sodium hydroxide,
c) the organic phase is separated off,
d) the organic phase is washed with hot water and
e) excess aniline is removed from the organic phase by distillation and the condensates are fed without further work-up to the collected wastewater (all wastewater from steps a)-d)), and having a content of 0.24% by weight of MDA, 33.8% by weight of aniline and 4.9% by weight of sodium chloride are heated via a heat exchanger to temperatures of >80° C. and worked up in a separation stage (step g)) and subsequently a two-stage extraction stage operated in countercurrent using MDA-free aniline as extractant. Here, the MDA-free aniline fed in at 1.5 t/h is heated to a temperature of >50° C. before being fed to the extraction stage,
the freshly used aniline and also the aniline leaving the first and second stages of the extraction stage are intensively mixed with an energy input of 0.1 kW/m$^3$ of wastewater with the wastewater conveyed in countercurrent or the mixture used, then separated off again in the settlers located downstream of the mixers at an average residence time of 20 minutes while maintaining a temperature of >80° C.

After the extraction of the wastewater, the wastewater contains <1 ppm of MDA and is likewise free of aminals and aminobenzylamines. Its aniline content of 3.1% by weight corresponds to the solution equilibrium.

For further work-up, the extracted wastewater is brought to a pH of 7.2 by means of 30% strength by weight hydrochloric acid, then fed to a removal of aniline by distillation, freed there of residual aniline and low boilers present at 450 mbar and 80° C., with the condensates obtained in the removal of aniline by distillation being passed to a further low boiler removal, and recirculated as dilution water to step b) and/or as washing water to step d) of the preparation of MDA.

The wastewater which leaves the removal of aniline by distillation at 5.6 t/h and has an NaCl content of 12.2% by weight is heated via a heat exchanger to 40° C., passed over an activated carbon control bed, then passed to the brine preparation of an NaCl electrolysis, with the solution fed to the brine preparation having a TOC value of 19 ppm.

The electrolysis is carried out in 302 cells each having an anode area of 2.71 m², with the current density being 4 kA/m², the cell potential being 2.0 V, the temperature at the outlet on the cathode side being 88° C. and the temperature at the outlet on the anode side being 89° C. The electrolysis cells are provided with a standard anode coating from Denora, Germany, membranes of the type N2010 from DuPont are used as ion exchange membranes and 200 kg/h of solution are circulated by pumping through the anode chambers of the cell and 75 kg/h are circulated by pumping through the cathode chambers of each cell. A gas diffusion electrode as described in DE 10 2005 023615 A1 is used as cathode.

The concentration of the NaCl solution fed into the anode chambers is 22% by weight of NaCl. A 15.1% strength solution is taken from the anode chambers. 0.406 t/h of this stream is discarded. The NaCl solution taken from the anode chambers is supplemented with 5.6 t/h of MDA wastewater having an NaCl content of 12.2%, 6.51 t/h of solid sodium chloride and 8.07 t/h of further water. The water transport through the membranes used is 5.3 mol of water per mol of sodium.

The concentration of the sodium hydroxide solution fed into the cathode sides is 30% by weight, and that of the sodium hydroxide solution taken from the cathode sides is 32.0% by weight. 15.26 t/h of the 32.0% strength by weight sodium hydroxide solution are taken from the outflow stream from the cathode side and the remainder is supplemented with 1.43 t/h of water and fed back to the cathode sides of the electrolysis cells. 1.458 t/h of 32% strength by weight NaOH are recirculated to the preparation of MDA and the remaining amount of sodium hydroxide solution is available for use in other processes.

Owing to the high water transport capacity of the membranes used, only very little additional dilution of the sodium hydroxide solution produced is required, the dilution is achieved predominantly by means of water transport through the membranes, 11.65 t/h of water are introduced via the membranes into the cathode sides, the entire water from the MDA wastewater is utilized in the electrolysis for diluting the sodium hydroxide solution produced in the electrolysis.

4.32 t/h of chlorine are reacted with CO over activated carbon at a CO excess of 7 mol % to form phosgene and converted into a 45% strength by weight solution of phosgene in monochlorobenzene.

20 t/h of a 30% strength by weight solution of an MDA prepared according to steps a)-e) and having an average molar mass of 224 g/mol in monochlorobenzene having a temperature of 80° C. and 26.7 t/h of a 45% strength by weight solution of phosgene in monochlorobenzene having a temperature of −5° C. are mixed and reacted continuously in a mixer reactor as described in EP-A-0 830 894 with a power input of 52 kW. The pressure in the mixer reactor is 13.5 bar.

After an average residence time of 2.1 sec in the mixer reactor, the reaction mixture is conveyed via the impeller of the mixer reactor into a subsequent tube reactor which is operated at 14 bar and can be heated by means of a heating jacket, maintained at >120° C. in this at a residence time of 120 sec and the reaction mixture is then depressurized via a regulating valve into a heatable reaction tower which is divided into chambers by means of perforated plates and is operated at a pressure at the top of 1.7 bar as phase separation apparatus.

The reaction mixture is fed in at the bottom of the reaction tower and on its way through the apparatus is heated uniformly by means of segment heating facilities so that the separately discharged gas phase and also the liquid phase leave the apparatus at a temperature of 115° C.

The gas phase taken off (18.65 t/h) contains a mixture of phosgene (5.64 t/h, 30.2% by weight), hydrogen chloride (4.37 t/h, 21.6% by weight), monochlorobenzene (8.97 t/h, 48.10% by weight) and small amounts of various low boilers (carbon tetrachloride, chloroform, nitrogen, carbon monoxide, carbon dioxide) and is fed to a hydrogen chloride/phosgene separation of a known type. 0.426 t/h of the hydrogen chloride which has been separated off and purified is taken up in 0.99 t/h of water and passed in the form of the resulting 30% strength by weight hydrochloric acid to the preparation of MDA as catalyst.

The liquid phase overflowing from the tower (28.05 t/h) contains MDI (7.55 t/h, 26.9% by weight), monochlorobenzene, phosgene and small amounts of dissolved hydrogen chloride; the liquid phase is freed by methods of the prior art of hydrogen chloride, phosgene and monochlorobenzene and after-treated thermally. The mixture of diisocyanates and polyisocyanates of the diphenylmethane series prepared in this way is characterized by the following product properties:

| | |
|---|---|
| viscosity/25° C.: | 49 mPa*s |
| NCO content | 31.7% |
| colour E 430 [1] | 0.134 |
| colour E 520 [1] | 0.026 |

[1] 1.0 g of the isocyanate obtained was dissolved in chlorobenzene and diluted with chlorobenzene to 50 ml. The absorbance of the resulting solution was determined at the two wavelengths 430 nm and 520 nm using a Dr. Lange LICO 300 Photometer.

Example 2

8.3 t/h of a mixture containing proportionately wastewater and condensates from the stages of a preparation of MDA in which f) aniline and formalin are reacted in an A/F ratio of 2.1 in the presence of 30% strength by weight hydrochloric acid as catalyst at a degree of protonation of 15%, g) the reaction mixture is neutralized with sodium hydroxide, h) the organic phase is separated off, i) the organic phase is washed with hot water and j) excess aniline is removed from the organic phase by distillation and the condensates are fed without further work-up to the collected wastewater (all wastewater from steps f)-i)), and having a content of 0.14% by weight of MDA, 16.2% by weight of aniline and 6.5% by weight of sodium chloride are heated via a heat exchanger to temperatures of >80° C. and worked up in a separation stage (step h)) and subsequently passed to a two-stage extraction stage operated in countercurrent using MDA-free aniline as extractant. Here the MDA-free aniline fed in at 1.0 t/h is heated to a temperature of >75° C. before being fed to the extraction stage, the freshly used aniline and also the aniline leaving the first and second stages of the extraction stage are intensively mixed with an energy input of >0.1 kW/m³ of wastewater with the wastewater conveyed in countercurrent or the mixture used, then separated off again in the settlers located downstream of the mixers at an average residence time of 20 minutes while maintaining a temperature of >80° C.

After the extraction of the wastewater, the wastewater contains <11.5 ppm of MDA and is likewise largely free of aminals and aminobenzylamines. Its aniline content of 3.1% by weight corresponds to the solution equilibrium.

For further work-up, the extracted wastewater is brought to a pH of 7.2 by means of 30% strength by weight hydrochloric acid, then fed to a removal of aniline by distillation, freed there of residual aniline and low boilers present at 450 mbar and 80° C., with the condensates obtained in the removal of aniline by distillation being passed to a further low boiler removal, and recirculated as dilution water to step g) and/or as washing water to step i) of the preparation of MDA.

The wastewater which leaves the removal of aniline by distillation at 4.98 t/h and has an NaCl content of 12.56% by weight is heated via a heat exchanger to 40° C., passed over an activated carbon control bed, then passed to the brine preparation of an NaCl electrolysis, with the solution fed to the brine preparation having a TOC value of 24 ppm.

The electrolysis is carried out in 115 cells each having an anode area of 2.71 $m^2$, with the cell potential being 2.0 V, the temperature at the outlet on the cathode side being 88° C. and the temperature at the outlet on the anode side being 89° C. The electrolysis cells are provided with a standard anode coating from Denora, Germany, membranes of the type N2010 from DuPont are used as ion exchange membranes and 200 kg/h of solution are circulated by pumping through the anode chambers of the cells and 75 kg/h are circulated by pumping through the cathode chambers of each cell. A gas diffusion electrode as described in DE 10 2005 023615 A1 is used as cathode.

The concentration of the NaCl solution fed into the anode chambers is 22% by weight of NaCl. A 15.1% strength solution was taken from the anode chambers and of this 0.155 t/h was taken off as purge, and the NaCl solution taken from the anode chambers was subsequently supplemented with 4.98 t/h of MDA wastewater having an NaCl content of 12.56%, 2.115 t/h of solid sodium chloride and 0.51 t/h of further water. The water transport through the membranes used is 5.2 mol of water per mol of sodium.

The concentration of the sodium hydroxide solution fed into the cathode sides is 30% by weight, and that of the sodium hydroxide solution taken from the cathode sides is 32.0% by weight. 5.775 t/h of the 32.0% strength by weight sodium hydroxide solution are taken from the outflow stream from the cathode side and the remainder is supplemented with 0.594 t/h of water and fed back to the cathode sides of the electrolysis cells. Owing to the high water transport capacity of the membranes used, only very little additional dilution of the sodium hydroxide solution produced is required, the dilution is achieved predominantly by means of water transport through the membranes, 4.355 t/h of water are introduced via the membranes into the cathode sides, the entire water from the MDA wastewater is utilized in the electrolysis for diluting the sodium hydroxide solution produced in the electrolysis 1.649 t/h of the chlorine produced in the NaCl electrolysis are admixed with 1.963 t/h of chlorine produced in a conventional HCl electrolysis according to the prior art and together reacted with CO over activated carbon at a CO excess of 7 mol % to form phosgene and converted into a 45% strength by weight solution of phosgene in monochlorobenzene. 16.67 t/h of a 30% strength by weight solution of an MDA prepared according to steps f)-j) and having an average molar mass of 232 g/mol in monochlorobenzene having a temperature of 80° C. and 22.22 t/h of a 45% strength by weight solution of phosgene in monochlorobenzene having a temperature of −5° C. are mixed and reacted continuously in a mixer reactor as described in EP-A-0 830 894 with a power input of 58 kW. The pressure in the mixer reactor is 13.8 bar.

After an average residence time of 2.5 sec in the mixer reactor, the reaction mixture is conveyed via the impeller of the mixer reactor into a subsequent tube reactor which is operated at 14.2 bar and can be heated by means of a heating jacket, maintained at >120° C. in this at a residence time of 120 sec and the reaction mixture is then depressurized via a regulating valve into a heatable reaction tower which is divided into chambers by means of perforated plates and is operated at a pressure at the top of 1.7 bar as phase separation apparatus.

The reaction mixture is fed in at the bottom of the reaction tower and on its way through the apparatus is fed uniformly by means of segment heating facilities so that the separately discharged gas phase and also the liquid phase leave the apparatus at a temperature of 114° C.

The gas phase taken off (15.70 t/h) contains a mixture of phosgene (4.68 t/h, 29.82% by weight), hydrogen chloride (3.60 t/h, 22.91% by weight), monochlorobenzene (7.42 t/h, 47.27% by weight) and small amounts of various low boilers (carbon tetrachloride, chloroform, nitrogen, carbon monoxide, carbon dioxide) and is fed to a hydrogen chloride/phosgene separation of a known type. 0.39 t/h of the hydrogen chloride which has been separated off and purified is taken up in 0.91 t/h of water and passed in the form of the resulting 30% strength by weight hydrochloric acid to the preparation of MDA as catalyst.

The liquid phase overflowing from the tower (23.19 t/h) contains MDI (6.25 t/h, 26.95% by weight), monochlorobenzene, phosgene and small amounts of dissolved hydrogen chloride; the liquid phase is freed by methods of the prior art of hydrogen chloride, phosgene and monochlorobenzene and after-treated thermally. The mixture of diisocyanates and polyisocyanates of the diphenylmethane series prepared in this way is characterized by the following product properties:

| | |
|---|---|
| viscosity/25° C.: | 132 mPa*s |
| NCO content: | 31.2% |
| colour E 430 [1] | 0.182 |
| colour E 520 [1] | 0.035 |

[1] 1.0 g of the isocyanate obtained was dissolved in chlorobenzene and diluted with chlorobenzene to 50 ml. The absorbance of the resulting solution was determined at the two wavelengths 430 nm and 520 nm using a Dr. Lange LICO 300 Photometer.

The invention claimed is:

1. A process for preparing methylenediphenyl diisocyanate, comprising
   A) reacting aniline with formaldehyde in the presence of hydrochloric acid as catalyst to form a mixture of diamines and polyamines of the diphenylmethane series (MDA) and subsequently at least partially neutralizing said hydrochloric acid with alkali metal hydroxide; wherein
      A1) water introduced with the starting materials or formed during the reaction of aniline with formaldehyde in the presence of hydrochloric acid as catalyst to form a mixture of diamines and polyamines of the diphenylmethane series (MDA) is at least partly removed from the reaction mixture;
      A2) after neutralization of the reaction mixture formed in A1), an aqueous solution comprising alkali metal chloride and an organic phase comprising said mixture of diamines and polyamines is obtained;

A3) the organic phase from A2) is separated off from the aqueous phase and worked up to give said mixture of diamines and polyamines; and A4) the aqueous solution comprising alkali metal chloride remaining after A3) is optionally at least partly combined with any water removed in A1) and/or with aqueous phases obtained in the work-up of said organic phase in step A3); purified; and at least partly fed to the electrochemical oxidation C); and wherein said aqueous solution comprising alkali metal chloride is adjusted to a pH of <8 prior to purification in A4);

B) reacting said mixture of diamines and polyamines of the diphenylmethane series with phosgene to form a mixture of diisocyanates and polyisocyanates of the diphenylmethane series (MDI) and hydrogen chloride;

wherein

C) the hydrochloric acid neutralized in A) is separated off in the form of a solution comprising alkali metal chloride and at least a portion of which is subsequently fed to an electrochemical oxidation to form chlorine, alkali metal hydroxide, and optionally hydrogen; and D) at least part of the chlorine formed in C) is used to prepare the phosgene used in B), wherein said aqueous solution comprising alkali metal chloride is adjusted to a TOC value of <200 ppm before the oxidation C).

2. The process of claim 1, wherein said alkali metal hydroxide in A) is sodium hydroxide.

3. The process of claim 1, wherein at least part of the alkali metal hydroxide formed in C) is recirculated to A) for neutralization of said hydrochloric acid.

4. The process of claim 1, wherein at least part of the hydrogen chloride formed in B) is converted into hydrochloric acid, at least part of which is used as said catalyst in A).

5. The process of claim 1, wherein the concentration of alkali metal chloride in the aqueous solution comprising alkali metal chloride formed in A) is from 2 to 24% by weight.

6. The process of claim 1, wherein the concentration of alkali metal chloride in the aqueous solution comprising alkali metal chloride formed in A) is from 5 to 15% by weight.

7. The process of claim 1, wherein said aqueous solution comprising alkali metal chloride is adjusted to an alkali metal chloride content of >5% by weight by removal of water and/or by addition of alkali metal chlorides in solid form or in the form of a concentrated solution before being used in an electrochemical oxidation.

8. The process of claim 1, wherein the aniline/formaldehyde reaction in A) is carried out at a degree of protonation of <30%.

9. The process of claim 1, wherein the electrochemical oxidation in C) is carried out as an alkali metal chloride electrolysis using ion exchange membranes and/or using gas diffusion electrodes as cathode.

10. The process of claim 9, wherein the alkali metal chloride electrolysis is carried out by the membrane electrolysis process using an ion exchange membrane, with the alkali metal chloride of the solution containing alkali metal chloride being sodium chloride and the ion exchange membrane having a water transport capacity of >3 mol of water/mol of sodium.

11. The process of claim 9, wherein the alkali metal chloride solutions fed to the alkali metal chloride electrolysis are adjusted to a pH of <7 prior to electrolysis.

12. The process of claim 9, wherein the concentration of alkali metal chloride in the solution comprising alkali metal chloride leaving the electrolysis cell is from 100 to 280 g/l.

13. The process of claim 9, wherein the concentration of the alkali metal hydroxide solution obtained from the electrolysis is from 13 to 33% by weight.

* * * * *